(12) United States Patent
Lopez-Berestein et al.

(10) Patent No.: US 7,220,853 B2
(45) Date of Patent: May 22, 2007

(54) INHIBITION OF CHRONIC MYELOGENOUS LEUKEMIC CELL GROWTH BY LIPOSOMAL-ANTISENSE OLIGODEOXY-NUCLEOTIDES TARGETING TO GRB2 OR CRK1

(75) Inventors: Gabriel Lopez-Berestein, Bellaire, TX (US); Ana M. Tari, Houston, TX (US); Ralph B. Arlinghaus, Bellaire, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 546 days.

(21) Appl. No.: 10/327,509

(22) Filed: Dec. 20, 2002

(65) Prior Publication Data

US 2003/0153526 A1    Aug. 14, 2003

Related U.S. Application Data

(63) Continuation of application No. 08/679,437, filed on Jul. 8, 1996.

(51) Int. Cl.
*C07H 21/04* (2006.01)
(52) U.S. Cl. .............. 536/24.5; 536/24.33; 536/24.31
(58) Field of Classification Search .............. 536/23.1, 536/24.5, 24.3, 24.31, 24.33; 514/44
See application file for complete search history.

(56) References Cited

U.S. PATENT DOCUMENTS

| | | | |
|---|---|---|---|
| 4,229,360 A | 10/1980 | Schneider et al. ........... 260/403 |
| 4,394,448 A | 7/1983 | Szoka, Jr. et al. ........... 435/172 |
| 4,469,863 A | 9/1984 | Ts'o et al. .................... 536/27 |
| 4,835,263 A | 5/1989 | Nguyen et al. ............... 536/27 |
| 4,837,028 A | 6/1989 | Allen .......................... 424/450 |
| 4,904,582 A | 2/1990 | Tullis ............................ 435/6 |
| 4,920,016 A | 4/1990 | Allen et al. ................. 424/450 |
| 5,094,785 A | 3/1992 | Law et al. .................... 264/4.3 |
| 5,188,897 A | 2/1993 | Suhadolnik et al. ..... 428/402.2 |
| 5,202,429 A | 4/1993 | Tsujimoto et al. ......... 536/23.5 |
| 5,225,326 A | 7/1993 | Bresser et al. ................. 435/6 |
| 5,279,833 A | 1/1994 | Rose .......................... 424/450 |
| 5,376,646 A | 12/1994 | Pittrof et al. ................. 514/78 |
| 5,378,825 A | 1/1995 | Cook et al. ............... 536/25.34 |
| 5,510,239 A * | 4/1996 | Baracchini et al. ............. 435/6 |
| 5,527,538 A | 6/1996 | Baldeschwieler .......... 424/1.21 |
| 5,585,479 A | 12/1996 | Hoke et al. ................. 536/24.5 |
| 5,661,018 A | 8/1997 | Ashley et al. ........... 435/172.3 |
| 5,665,710 A | 9/1997 | Rahman et al. ............... 514/44 |
| 5,696,248 A | 12/1997 | Peyman et al. ............ 536/22.1 |
| 5,705,385 A | 1/1998 | Bally et al. .............. 435/320.1 |
| 5,734,033 A | 3/1998 | Reed .......................... 536/23.1 |
| 5,734,039 A * | 3/1998 | Calabretta et al. ......... 536/24.5 |
| 5,750,669 A | 5/1998 | Rosch et al. ............... 536/24.3 |
| 5,831,048 A * | 11/1998 | Schweighoffer et al. ... 536/23.1 |
| 5,831,066 A | 11/1998 | Reed .......................... 536/24.5 |
| 5,874,224 A | 2/1999 | Bandman et al. ............... 435/6 |
| 5,891,714 A | 4/1999 | Ashley et al. ........... 435/320.1 |
| 5,908,635 A | 6/1999 | Thierry ...................... 424/450 |
| 5,976,567 A | 11/1999 | Wheeler et al. ............ 454/450 |
| 6,015,886 A | 1/2000 | Dale et al. ................. 536/23.1 |
| 6,034,235 A | 3/2000 | Sugiyama et al. ......... 536/24.5 |
| 6,040,181 A | 3/2000 | Reed .......................... 435/377 |
| 6,096,720 A | 8/2000 | Love et al. ................... 514/44 |
| 6,110,490 A | 8/2000 | Thierry ...................... 424/450 |
| 6,120,794 A | 9/2000 | Liu et al. .................... 424/450 |
| 6,120,798 A | 9/2000 | Allen et al. ................. 424/450 |
| 6,126,965 A | 10/2000 | Kasid et al. ................ 424/450 |
| 6,136,965 A | 10/2000 | Bruice et al. .............. 536/25.3 |
| 6,211,162 B1 | 4/2001 | Dale et al. .................... 514/44 |
| 6,211,349 B1 | 4/2001 | Dale et al. ................. 536/23.1 |
| 6,277,832 B1 | 8/2001 | Sugiyama et al. ............ 514/44 |
| 6,277,981 B1 | 8/2001 | Tu et al. .................... 536/25.3 |
| 6,291,668 B1 | 9/2001 | Ziegler et al. ............. 536/24.5 |
| 6,326,487 B1 | 12/2001 | Peyman et al. ............ 536/24.5 |

FOREIGN PATENT DOCUMENTS

| | | |
|---|---|---|
| CA | 2113494 | 7/1995 |
| WO | WO 88/04924 | 7/1988 |
| WO | WO 95/09236 | 4/1995 |
| WO | WO 95/31545 | 11/1995 |
| WO | WO 97/20573 | 6/1997 |
| WO | WO 00/40595 | 7/2000 |
| WO | WO 02/17852 | 3/2002 |

OTHER PUBLICATIONS

Bonati et al. Antisense modulation of the GBR2 gene inhibits clonogenic K562 leukemic cells. Blood, 86(10S1): 725A, 1995.*
Lowenstein et al. The SH2 and SH3 Domain-Containing Protein GRB2 Links Receptor Tyrosine Kinases to ras Signaling. Cell, 70:431-442, 1992. Cell Press.*
Wang et al. Highly Efficient DNA Delivery Mediated by pH-Sensitive Immunoliposomes. Biochemistry, 28: 9508-9514, 1989, American Chemical Society.*
ten Hoeve et al. Cellular Interactions of CRKL, an SH2-SH3 Adaptor Protein. Cancer 54: 2563-2567, 1994.*
Weintraub, H. Antisense RNA and DNA. Scientific American 1990: 40-46.*
Puil et al. Bcr-Abl oncoproteins bind directly to activators of the Ras signaling pathway. EMBO Journal 1994, vol. 13, No. 4:764-773.*

(Continued)

*Primary Examiner*—Sean McGarry
*Assistant Examiner*—Kimberly Chong
(74) *Attorney, Agent, or Firm*—Fulbright & Jaworski L.L.P.

(57) ABSTRACT

The present invention provides novel compositions and methods for use in the treatment of cancer, specifically, in the treatment of chronic myelogenous leukemia (CML). The compositions contain antisense oligonucleotides that hybridize to Grb2 and Crkl nucleic acids, the gene products of which are known to interact with the tumorigenic protein bcr-abl. Used alone, in conjunction with each other, and even in conjunction with antisense oligonucleotides directed to bcr-abl nucleic acids, these compositions inhibit the proliferation of CML cancer cells.

5 Claims, 5 Drawing Sheets

OTHER PUBLICATIONS

Baichwal and Sugden, "Vectors for Gene Transfer Derived from Animal DNA Viruses: Transient and Stable Expression of Transferred Genes," *In: Gene Transfer*, Kucherlapati (Ed.), New York: Plenum Press, 1986.

Bangham et al., "Diffusion of Univalent Ions Across the Lamellae of Swollen Phospholipids," *J. Mol. Biol.*, 13:238-252, 1965.

Bedi et al., "Inhibition of Apoptosis by BCR-ABL in Chronic Myeloid Leukemia," *Blood*, 38(9):2038-2044, 1994.

Benvenisty and Reshef, "Direct Introduction of Genes into Rats and Expression of the Genes," *Proc. Natl. Acad. Sci. USA*, 83:9551-9555, 1986.

Bonati et al., "Anti-sense modulation of the GRB2 gene inhibits clonogenic K562 leukemic cells," *Blood*, 86(10S1):725A, 1995.

Calabretta et al., "Antisense strategies in the treatment of leukemias," *Seminars in Oncology*, 23:78-87, 1996.

Chang et al., "Foreign Gene Delivery and Expression in Hepatocytes Using a Hepatitis B Virus Vector," *Hepatology*, 14(4, Pt. 2):124A, 1991.

Chen and Okayama, "High-Efficiency Transformation of Mammalian Cells by Plasmid DNA," *Mol. Cell. Biol.*, 7(8):2745-2752, 1987.

Coffin, "Retroviridae and their Replication," *In: Virology*, 2nd Edition, Fields et al. (Eds.), New York: Raven Press, pp. 1437-1500, 1990.

Coupar et al., "A General Method for theConstruction of Recombinant Vaccinia Viruses Expressing Multiple Foreign Genes," *Gene*, 68:1-10, 1988.

Dubensky et al., "Direct Transfection of Viral and Plasmid DNA into the Liver or Spleen of Mice," *Proc. Natl. Acad. Sci. USA*, 81:7529-7533, 1984.

Fechheimer et al., "Transfection of Mammalian Cells with Plasmid DNA by Scrape Loading and Sonication Loading," *Proc. Natl. Acad. Sci., USA*, 84:8463-8467, 1987.

Fraley et al., "Entrapment of a Bacterial Plasmid in Phospholipid Vesicles: Ptoential for Gene Transfer," *Proc. Natl. Acad. Sci., USA*, 76(7):3348-3352, 1979.

Friedmann, "Progress Toward Human Gene Therapy," *Science*, 244:1275-1281, 1989.

Gewirtz et al., "Facilitating oligonucleotide delivery: helping antisense deliver on its promise," *Proc. Natl. Acad. Sci., USA*, 93:3161-3163, 1996.

Ghosh and Bachhawat, "Targeting of Liposomes to Hepatocytes," *In: Liver Diseases, Targeted Diagnosis and Therapy Using Specific Receptors and Ligands*, Wu and Wu (Eds.), New York: Marcel Dekker, pp. 87-103, 1991.

Gopal, "Gene Transfer Method for Transient Gene Expression, Stable Transformation, and Cotransformation of Suspension Cell Cultures," *Mol. Cell. Biol.*, 5(5):1188-1190, 1985.

Graham and van der Eb, "A New Technique for the Assay of Infectivity of Human Advenovirus 5 DNA," *Virology*, 52:456-467, 1973.

Graham et al., "Characteristics of a Human Cell Line Transformed by DNA from Human Adenovirus Type 5," *J. Gen. Virol*, 36:59-72, 1977.

Gregoriadis, "Liposomes," *In: Drug Carriers in Biology and Medicinè*, Gregoriadis (Ed.), New York: Academic Press, pp. 287-341, 1979.

Grunhaus and Horwitz, "Adenoviruses as Cloning Vectors," *Seminar in Virology*, 3:237-252, 1992.

Harland and Weintraub, "Translation of mRNA Injected into Xenopus Oocytes is Specifically Inhibited by Antisense RNA," *J Cell Biology*, 101:1094-1099, 1985.

Hermonat and Muzyczka, "Use of Adeno-Associated Virus as a Mammalian DNA Cloning Vector: Transduction of Neomycin Resistance into Mammalian Tissue Culture Cells," *Proc. Natl. Acad. Sci., USA*, 81:6466-6470, 1984.

Horwich et al., "Synthesis of Hepadnavirus Particles that Contain Relication-Defective Duck Hepatitis B Virus Genomes in Cultured HuH7 Cells," *J Virology*, 64(2):642-650, 1990.

International Search Report dated Nov. 18, 1997 (UTFC:483P).

James, "Towards gene inhibition therapy: a review of progress and prospects in the field on antiviral antisense nucleic acids and ribozymes," *Antiviral Chemistry and Chemotherapy*, 2:191-214, 1991.

Kaneda et al., "Increased Expression of DNA Cointroduced with Nuclear Protein in Adult Rat Liver," *Science*, 243:375-378, 1989.

Kato et al., "Expression of Hepatitis B Virus Surface Antigen in adult Rat Liver," *J. Biol. Chem.*, 266(6):3361-3364, 1991.

Klein et al., "High-Velocity Microprojectiles for Delivering Nucleic Acids into Living Cells," *Nature*, 327:70-73, 1987.

Lebleu et al., "Controle de l'expression genetique par des acides nucleiques anti-sens," *C.R. Soc. Biol.*, 186:560-566, 1992.

Lowenstein et al., "The SH2 and SH3 Domain-Containing Protein GRB2 Links Receptor Tyrosine Kinases to ras Signaling," *Cell*, 70:431-442, 1992.

Mann et al., "Construction ofa Retrovirus Packaging Mutant and its Use to Produce Helper-Free Defective Retrovirus," *Cell*, 33:153-159, 1983.

McGahon et al., "BCR-ABL Maintains Resistance of Chronic Myelgenous Leukemia Cells to Apoptotic Cell Death," *Blood*, 83(5):1179-1187, 1994.

Mulligan et al., "The basic science of gene therapy," *Science*, 260:926-932, 1993.

Nicolas and Rubenstein, "Retroviral Vectors," *In: Vectors: A Survey of Molecular Cloning Vectors and Their Uses*, Rodriguez and Denhardt (Eds.), Stoneham, MA: Butterworth, 1988.

Nicolau and Sene, "Liposome-Mediated DNA Transfer in Eukaryotic Cells. Dependence of the Transfer Efficiency Upon the Type of Liposomes Used and the Host Cell Cycle Stage," *Biochimica et Biophysica Acta*, 721:185-190, 1982.

Nicolau et al., "Liposomes as Carriers for In Vivo Gene Transfer and Expression," *Methods Enzymol.*, 149:157-176, 1987.

Paskind et al., "Dependence of Moloney Murine Leukemia Virus Production on Cell Growth," *Virology*, 67:242-248, 1975.

Pendergast et al., "BCR-ABL-Induced Oncogenesis is Mediated by Direct Interaction with the SH2 Domain o the GRB-2 Adaptor Protein," *Cell*, 75:175-187, 1993.

Potter, "Enhancer-Dependent Expression of Human κ Immunoglobulin Genes Introduced into Mouse Pre-Lymphocytes by Electroporation," *Proc. Natl. Acad. Sci. USA*, 81:7161-7165, 1984.

Puil et al., "Bcr-Abl Oncoproteins Bind Directly to Activators of the Ras Signalling Pathway," *EMBO J*, 13(4):764-773, 1994.

Ridgway, "Mammalian Expression Vectors," *In: Vectors: A Survey of Molecular Cloning Vectors and Their Uses*, Rodriguez and Denhardt (Eds.), Stoneham, MA: Butterworths, 1988.

Rippe et al., "DNA-Mediated Gene Transfer into Adult Rat Hepatocytes in Primary Culture," *Mol. Cell. Biol*, 10(2):689-695, 1990.

Skorski et al., "Negative Regulation of p120GAP GTPase Promoting Activity by $p210^{ber/abl}$, Implication for RAS-Dependent Philadelphia Chromosome Positive Cell Growth," *J. Exp. Med.*, 179:1855-1865, 1994.

Skorski et al., "Phosphatidylinositol-3 Kinase Activity is Regulated by BCR/ABL and is Required for the Grwoth of Philadelphia Chromosome-Positive Cells," *Blood*, 86(2):726-736, 1995.

Skorski et al., "Suppression of Philadelphia[1] Leukemia Cell Growth in Mice by BCR-ABL Antisense Oligodeoxynucleotide," *Proc. Natl. Acad. Sci., USA*, 91:4504-4508, 1994.

Stratford-Perricaudet and Perricaudet, "Gene Transfer Into Animals: The Promise of Adenovirus," *In: Human Gene Transfer*, Cohen-Haguenauer and Boiron (Eds.), John Libbey Eurotext Ltd., 219:51-61, 1991.

Szczylik et al., "Selective Inhbiition of Leukemia Cell Proliferation by BCR-ABL Antisense Oligodeoxynucleotides," *Science*, 253:562-565, 1991.

Tari et al., "Inhibition of GRB2 and CRKL proteins result in growth inhibition of Philadelphia chromosome positive leukemic cells," *Biochem. Biophys. Res. Comm.*, 235(2):383-388, 1997.

Tari et al., "Liposomal Delivery of Methylphosphonate Antisense Oligodeoxynucleotides in Chronic Myelogenous Leukemia," *Blood*, 84(2):601-607, 1994.

Temin, Retrovirus Vectors for Gene Transfer: Efficient Integration into and Expression of Exogenous DNA in Vertebrate Cell Genomes, *In: Gene Transfer*, Kucherlapati (Ed.), New York: Plenum Press, 1986.

ten Hoeve et al., "Cellular Interactions of CRKL, an SH2-SH3 Adaptor Protein," *Cancer Research*, 54:2563-2567, 1994.

ten Hoeve et al., "Isolation and Chromosomal Localization of CRKL, a Human crk-Like Gene," *Oncogene*, 8:2409-2414, 1993.

ten Hoeve et al., "Tyrosine Phosphorylation of CRKL in Philadelphia Leukemia," *Blood*, 84(6):1731-1736, 1994.

Tseng et al., "Antisense oligonucleotide technology in the development of cancer therapeutics," *Cancer Gene Therapy*, 1:65-71, 1994.

Tur-Kaspa et al., "Use of Electroporation to Introduce Biologically Active Foreign Genes in to Primary Rat Hepatocytes," *Mol. Cell. Biol.*, 6(2):716-718, 1986.

Uhlmann et al., "Antisense oligonucleotides: a new therapeutic principle," *Chem. Rev.*, 90:543-584, 1990.

Wagner et al., "Antisense Gene Inhibition by Oligonucleotides Containing C-5 Proopyne Pyrimidines," *Science*, 260:1510-1513, 1993.

Weiss, "Upping the antisense ante, scientist bet on profits form reverse genetics," *Science News*, 139:108-109, 1991.

Westermann et al., "Inhibition of expression of SV-40 virus large T-antigen by antisense oligodeoxyribonucleotides," *Biomed. Biochem. Acta.*, 48:85-93, 1989.

Wong et al., "Appearance of β-Lactamase Activity in Animal Cells Upon Liposome-Mediated Gene Transfer," *Gene*, 10-87-94, 1980.

Wu and Wu, "Evidence for Targeted Gene Delivery to Hep G2 Hepatoma Cells in Vitro," *Biochemistry*, 27:887-892, 1988.

Wu and Wu, "Receptor-Mediated In Vitro Gene Transformation by a Soluble DNA Carrier System," *J Biol. Chem*, 262(10):4429-4432, 1987.

Yang et al., "In Vivo and In Vitro Gene Transfer to Mammalian Somatic Cells by Particle Bombardment," *Proc. Natl. Acad. Sci., USA*, 87:9568-9572, 1990.

Zelenin et al., "High-Velocity Mechanical DNA Transfer of the Chloramphenioocolacetyl Transferase Gene Into Rodent Liver, Kidney and Mammary Gland Cells in Organ Explants and In Vivo," *FEBS*, 280(1):94-96, 1991.

\* cited by examiner

```
        GCCAGTGAATTCGGGGGCTCAGCCCTCCTCCCTCCCTTCCCCCTGCTTCAGGCTGCTGAG   60

CACTGAGCAGCGCTCAGAATGGAAGCCATCGCCAAATATGACTTCAAAGCTACTGCAGAC  120
                         M  E  A  I  A  K  Y  D  F  K  A  T  A  D    14

GACGAGCTGAGCTTCAAAAGGGGGGACATCCTCAAGGTTTTGAACGAAGAATGTGATCAG  180
SH3     D  E  L  S  F  K  R  G  D  I  L  K  V  L  N  E  E  C  D  Q   34

AACTGGTACAAGGCAGAGCTTAATGGAAAAGACGGCTTCATTCCCAAGAACTACATAGAA  240
        N  W  Y  K  A  E  L  N  G  K  D  G  F  I  P  K  N  Y  I  E   54

ATGAAACCACATCCGTGGTTTTTTGGCAAAATCCCCAGAGCCAAGGCAGAAGAAATGCTT  300
        M  K  P  H  P  W  F  F  G  K  I  P  R  A  K  A  E  E  M  L   74

AGCAAACAGCGGCACGATGGGGCCTTTCTTATCCGAGAGAGTGAGAGCGCTCCTGGGGAC  360
        S  K  Q  R  H  D  G  A  F  L  I  R  E  S  E  S  A  P  G  D   94

TTCTCCCTCTCTGTCAAGTTTGGAAACGATGTGCAGCACTTCAAGGTGCTCCGAGATGGA  420
SH2     F  S  L  S  V  K  F  G  N  D  V  Q  H  F  K  V  L  R  D  G  114

GCCGGGAAGTACTTCCTCTGGGTGGTGAAGTTCAATTCTTTGAATGAGCTGGTGGATTAT  480
        A  G  K  Y  F  L  W  V  V  K  F  N  S  L  N  E  L  V  D  Y  134

CACAGATCTACATCTGTCTCCAGAAACCAGCAGATATTCCTGCGGGACATAGAACAGGTG  540
        H  R  S  T  S  V  S  R  N  Q  Q  I  F  L  R  D  I  E  Q  V  154

CCACAGCAGCCGACATACGTCCAGGCCCTCTTTGACTTTGATCCCCAGGAGGATGGAGAG  600
        P  Q  Q  P  T  Y  V  Q  A  L  F  D  F  D  P  Q  E  D  G  E  174

CTGGGCTTCCGCCGGGGAGATTTTATCCATGTCATGGATAACTCAGACCCCAACTGGTGG  660
SH3     L  G  F  R  R  G  D  F  I  H  V  M  D  N  S  D  P  N  W  W  194

AAAGGAGCTTGCCACGGGCAGACCGGCATGTTTCCCCGCAATTATGTCACCCCCGTGAAC  720
        K  G  A  C  H  G  Q  T  G  M  F  P  R  N  Y  V  T  P  V  N  214

CGGAACGTCTAAGAGTCAAGAAGCAATTATTTAAAGAAAGTGAAAAATGTAAAACACATA  780
        R  N  V                                                     217

CAAAAGAATTAAACCCACAAGCTGCCTCTGACAGCAGCCTGTGAGGGAGTGCAGAACACC  840
        TGGCCGGGTCACCCTGTGACCCTCTCACTTTGGTTGGAACTTTAGGGGGTGGGAGGGGGC  900
        GTTGGATTTAAAAATGCCAAAACTTACCTATAAATTAAGAAGAGTTTTTATTACAAATTT  960
        TCACTGCTGCTCCTCTTTCCCCTCCTTTGTCTTTTTTTTCATCCTTTTTTCTCTTCTGTC 1020
        CATCAGTGCATGACGTTTAAGGCCACGTATAGTCCTAGCTGACGCCAATAATAAAAAACA 1080
        AGAAACCAAAAAAAAAAAAACCCGAATTCA                               1109
```

FIG. 4

```
   1  CGGAGGGGGAGGTGGCTGCCGCTTCTCCCGCGTCCGCCATTTTGTTGCTGTGGCTATTGGGAACAAGCTGGGCAAAAGCACCCCGGAGG

90  CGCGACGCTCCTTCGAGTTCGGTGCCTCGTGTGACGGCGGGGGTCGGTGAAGACCCGTCGAGCTGCGGCGCCGGCGCGTTCCAGGCCGGG

180  AGTCACTGGAGGCACCCCTGGGACGCCGAGCAGCCCGAGAACCCCGGGGTGGCCTCCGCTGCGGCTCGGGTTTGCCTGCCCCGACCCCCC

270  GGCTCTGCCGTGCATTCCCGGGCGGCTCTCTCCGTGTGGCGGCCCCGGAGCAGGCGGGCGGCGTCGGAGGATGCTGCGGGCCCGGAGCCG

360  AGAGGAAAGTGCTGGCCCAGCCCTCTGAGCGCTCCTCGAGGTGTGCGAGAGGCCCTTCCTCGGCCCCAAAGCCGTCTGCCGGGCTAAGGC

450  GTGCAGAGCAGGCGAGGACAGCCGCCGCCCCTACCGCCGCAGAGTCCCCGGTCCAACACCATGTCCTCCGCCAGGTTCGACTCCTCGGAC
   1                                                                  M  S  S  A  R  F  D  S  S  D

540  CGCTCCGCCTGGTATATGGGGCCGGTGTCTCGCCAGGAGGCGCAGACCCGGCTCCAGGGCCAGCGCCACGGTATGTTCCTCGTCCGCGAT
  11   R  S  A  W  Y  M  G  P  V  S  R  Q  E  A  Q  T  R  L  Q  G  Q  R  H  G  M  F  L  V  R  D     SH2

630  TCTTCCACCTGCCCTGGGGACTATGTGCTGTCGGTGTCCGAGAACTCGCGGGTCTCCCACTACATTATCAACTCGCTGCCCAACCGCCGT
  41   S  S  T  C  P  G  D  Y  V  L  S  V  S  E  N  S  R  V  S  H  Y  I  I  N  S  L  P  N  R  R

720  TTTAAGATCGGGGACCAGGAATTTGACCATTTGCCGGCCCTGCTGGAGTTTTACAAGATCCACTACCTGGACACCACCACCCTCATCGAG
  71   F  K  I  G  D  Q  E  F  D  H  L  P  A  L  L  E  F  Y  K  I  H  Y  L  D  T  T  T  L  I  E     SH2

810  CCTGCGCCCAGGTATCCAAGCCCACCAATGGGATCTGTCTCAGCACCCAACCTGCCTACAGCAGAAGATAACCTGGAATATGTACGGACT
 101   P  A  P  R  Y  P  S  P  P  M  G  S  V  S  A  P  N  L  P  T  A  E  D  N  L  E  Y  V  R  T

900  CTGTATGATTTTCCTGGGAATGATGCCGAAGACCTGCCCTTTAAAAAGGGTGAGATCCTAGTGATAATAGAGAAGCCTGAAGAACAGTGG
 131   L  Y  D  F  P  G  N  D  A  E  D  L  P  F  K  K  G  E  I  L  V  I  I  E  K  P  E  E  Q  W     SH3

990  TGGAGTGCCCGGAACAAGGATGGCCGGGTTGGGATGATTCCTGTCCCTTATGTCGAAAAGCTTGTGAGATCCTCACCACACGGAAAGCAT
 161   W  S  A  R  N  K  D  G  R  V  G  M  I  P  V  P  Y  V  E  K  L  V  R  S  S  P  H  G  K  H

1080  GGAAATAGGAATTCCAACAGTTATGGGATCCCAGAACCTGCTCATGCATACGCTCAACCTCAGACCACAACTCCTCTACCTGCAGTTTCC
 191   G  N  R  N  S  N  S  Y  G  I  P  E  P  A  H  A  Y  A  Q  P  Q  T  T  T  P  L  P  A  V  S

1170  GGTTCTCCTGGGGCAGCAATCACCCCTTTGCCATCCACACAGAATGGACCTGTCTTTGCGAAAGCAATCCAGAAAAGAGTACCCTGTGCT
 221   G  S  P  G  A  A  I  T  P  L  P  S  T  Q  N  G  P  V  F  A  K  A  I  Q  K  R  V  P  C  A     SH3

1260  TATGACAAGACTGCCTTGGCATTAGAGGTTGGTGACATCGTGAAAGTCACAAGGATGAATATAAATGGCCAGTGGGAAGGCGAAGTGAAC
 251   Y  D  K  T  A  L  A  L  E  V  G  D  I  V  K  V  T  R  M  N  I  N  G  Q  W  E  G  E  V  N

1350  GGGCGCAAAGGGCTTTTCCCCTTTACGCACGTCAAAATCTTTGACCCTCAAAACCCAGATGAAAACGAGTGATTGCTGTTGCCCTGTTTC
 281   G  R  K  G  L  F  P  F  T  H  V  K  I  F  D  P  Q  N  P  D  E  N  E

1440  CTGCTGCTTTGTTGTTCTGCCTGTCCTAGTCTCCTTTGAAGTGGGAAAGCATTTTCTCTCATAGGCAAGTCACACTGCATTGCCGAAGTC

1530  CAGCTTTCTGCAGACTGGCAGTCGCACACACATTTGGAATGCACACAGCGGCTGCCTCCTGATGTTTGTATCATAGTCGTATTGTGCAAA

1620  GAGTAGCCGATTTTAGAGTTCTTTTGGATCATAAACTGGAAATACTGATGGAAGCACACAAGTGGAGAGAAGTTGACGTGGAAAGGGTCT

1710  TCCTTCTCATTGCTGCCCGTTTGTACATGGGACTGATTCTGTCGTGTTCACCAGAGAAAGCTTGAGGCCATGGCGAGATACTGCATGTTT

1800  GCTGTTCCACAAAGCAGTGGCTTAGCTGCCATCTTGCTTTTCTTTGGACAACAGGAAGTGAACCTTAAGGAAGAGAGAATTC
```

FIG. 5

INHIBITION OF CHRONIC MYELOGENOUS LEUKEMIC CELL GROWTH BY LIPOSOMAL-ANTISENSE OLIGODEOXY-NUCLEOTIDES TARGETING TO GRB2 OR CRK1

This is a continuation of co-pending application Ser. No. 08/679,437, filed Jul. 8, 1996.

BACKGROUND OF THE INVENTION

A. Field of the Invention

The present invention relates to the field of cancer therapy, specifically, the treatment of chronic myelogenous leukemia. More particularly, these treatments involve the use of antisense oligonucleotides and liposomal formulations thereof.

B. Related Art

Chronic myelogenous leukemia (CML) is a hematologic malignancy in which uncontrolled proliferation of granulocytes occurs. It often is characterized by the reciprocal translocation of chromosomes 9 and 22, which relocates the Ableson (abl) protooncogene onto the 3'-end of the breakpoint cluster region (bcr). This produces a chimeric bcr-abl gene encoding a $p210^{bcr-abl}$ fusion protein, which is tumorigenic and is necessary for the growth of CML cells (Szczylik et al., 1991; Skorski et al., 1994; Tari et al., 1994; McGahon et al., 1994; Bedi et al., 1994).

The bcr-abl protein can autophosphorylate at the 177 tyrosine amino acid found within the first exon of bcr. When phosphorylated, the bcr domain of the bcr-abl protein binds to the SH2 domain of the growth factor receptor-bound protein 2 (Grb2) adaptor protein. Through the SH3 domain, Grb2 binds to the human Son of sevenless 1 (hSos1) GDP/GTP exchange factor resulting in ras protein activation. The bcr-abl protein can also transphorylate the 177 tyrosine amino acid found within the normal bcr protein. It is believed that when the normal bcr protein becomes tyrosine phosphorylated at amino acid 177, it also will complex with Grb2. When the bcr-abl protein is expressed, the p46 and p52 Shc (Puil et al., 1994) proteins become tyrosine phosphorylated as well. These Shc proteins have also been shown to form stable complexes with Grb2. Therefore, Grb2 appears to play a very important role in the tumorigenicity mediated by the bcr-abl protein (Puil et al., 1994; Pendergast et al., 1993).

Another adaptor protein, Crk-like (Crkl), also has been found to bind to bcr-abl. Unlike Grb2, Crkl binds to bcr-abl through the abl domain. Through its SH3 domain, Crkl can also bind to hSos1, which again leads to Ras protein activation (ten Hoeve et al., 1994a and 1994b). Thus, via the Grb2 and Crkl adaptor proteins, the bcr-abl protein has been linked to ras activation, which is known to lead to tumorigenesis. When ras protein expression is inhibited, proliferation of CML cells is also inhibited. Therefore, one of the major pathways in which bcr-abl protein promotes CML proliferation is by activating ras protein (Skorski et al., 1994 and 1995).

Liposomal-antisense oligonucleotides targeted to bcr-abl can reduce proliferation of CML cells. After maximal inhibition (75% growth inhibition and 90% protein inhibition), CML cells can still recover and grow if the liposomal-antisense oligonucleotides are removed from the culture medium. This is likely caused by incomplete inhibition of bcr-abl protein synthesis Tari et al., 1994). Thus, despite the ability of antisense oligonucleotides to inhibit proliferation of CML cells, there remains a need for more effective compositions and treatments against this form of cancer.

SUMMARY OF THE INVENTION

The present invention is designed to overcome the shortcomings of the prior art by providing improved compositions and methods for the treatment of CML. In particular, the present invention makes use of novel antisense oligonucleotides to target specific nucleic acids in the cells of CML patients.

Thus, in one embodiment, there is provided a composition comprising a polynucleotide that hybridizes to a Grb2-encoding polynucleotide. In another embodiment, there is provided a composition comprising a polynucleotide that hybridizes to a Crkl-encoding polynucleotide. These polynucleotides may be oligonucleotides having a length of 8–50 bases. In a further embodiment, the polynucleotide hybridizes to the translation initiation site of Grb2 mRNA or Crkl mRNA. In specific embodiments, the polynucleotide is an oligonucleotide having the sequence ATATTTGGCGATG-GCTTC (SEQ ID NO: 5) or GTCGAACCGGCGGAGGA (SEQ ID NO: 6). In another embodiment, the polynucleotide is encapsulated in a liposome. The liposome may advantageously be comprised of the lipid dioleoylphosphatidylcholine.

In yet another embodiment, there is provided a composition comprising (i) a polynucleotide that hybridizes to a Grb2-encoding polynucleotide or (ii) a polynucleotide that hybridizes to a Crkl-encoding polynucleotide. The composition may further comprise a polynucleotide that hybridizes to a bcr-abl-encoding polynucleotide.

In still yet another embodiment, there is provided a composition comprising an expression construct that encodes a first polynucleotide that hybridizes to a Grb2-encoding polynucleotide, wherein said first polynucleotide is under the control of a promoter that is active in eukaryotic cells. Similarly, there is provided a composition comprising an expression construct that encodes a first polynucleotide that hybridizes to a Crkl-encoding polynucleotide, wherein said first polynucleotide is under the control of a promoter that is active in eukaryotic cells.

In still yet another embodiment, there is provided a method for inhibiting proliferation of a cancer cell comprising contacting said cancer cell with a composition comprising at least (i) a polynucleotide that hybridizes to a Grb2 nucleic acid or (ii) a polynucleotide that hybridizes to a Crkl nucleic acid. The polynucleotides may be oligonucleotides having a length of 8–50 bases. The method may further comprise contacting the cancer cell with a composition comprising a polynucleotide that hybridizes to a bcr-abl nucleic acid. The composition may comprise both (i) a polynucleotide that hybridizes to a Grb2 nucleic acid or (ii) a polynucleotide that hybridizes to a Crkl nucleic acid.

The above method may be applied advantageously to a cancer cell that is a leukemia cell or, more specifically, a chronic myelogenous leukemia cell. The composition may comprise a liposome in which the polynucleotide is encapsulated. In a specific embodiment, the contacting takes place in a patient. The patient may be a human. The composition may advantageously be delivered to a human patient in a volume of 0.50–10.0 ml per dose or in an amount of 5–30 mg polynucleotide per $m^2$. In a particular regimen, the composition is administered three times per week for eight weeks.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 4: cDNA and Protein Sequence of GRB2. 5'- and 3'-untranslated flanking sequences are illustrated along with the coding region and amino acid sequence. SH2 (thick line) and SH3 (thin line) domains are indicated (SEQ ID NO: 1).

FIG. 5: cDNA and Protein Sequence of CRKL. 5'- and 3'-untranslated flanking sequences are illustrated along with the coding region and amino acid sequence. SH2, SH2', SH3 and SH4 domains are indicated by underlining (SEQ ID NO: 2).

DETAILED DESCRIPTION OF THE PREFERRED EMBODIMENTS

A. The Present Invention

Figure 1:
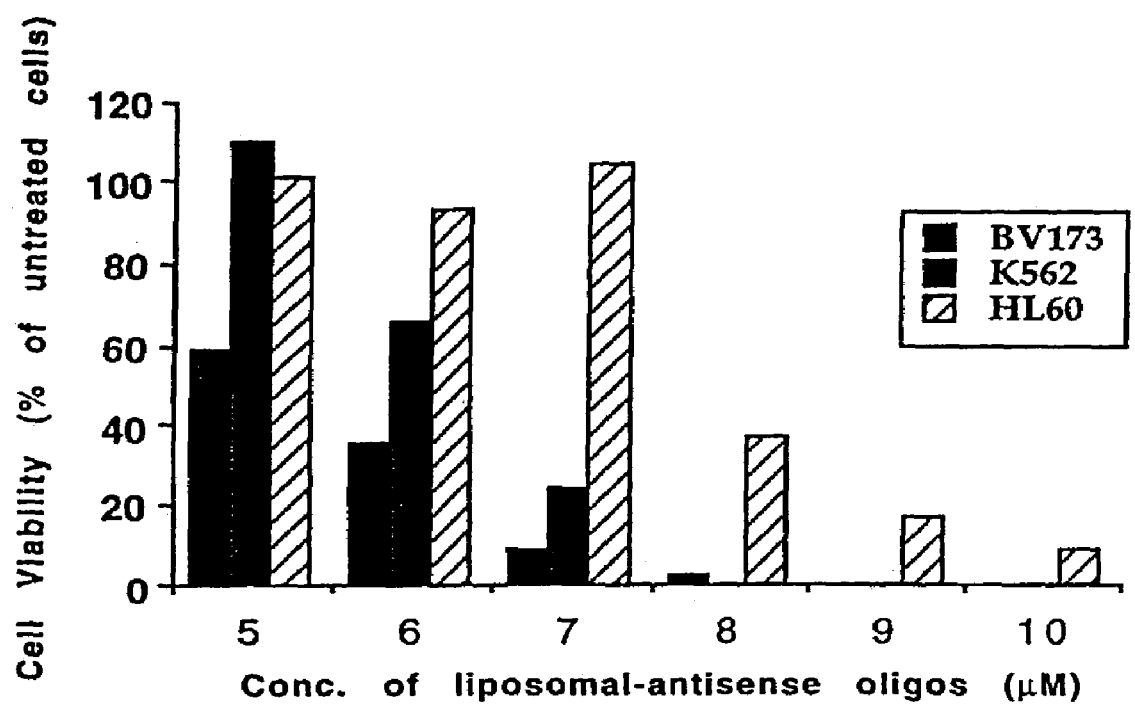
FIG. 1: Effects of Liposomal Antisense Oligonucleotides Specific for Grb2 on Leukemic Cell Growth. BV173, K562 and HL60 cells were incubated with increasing concentrations of liposomal-antisense oligonucleotides specific for Grb2. After three days of incubation, an alamarBlue assay was done to determine the growth-inhibitory effects of these oligonucleotides on the leukemic cells. Viability was expressed as a percentage of untreated cells, which was determined by (absorbance of treated cells/absorbance of untreated cells)×100.

Chronic myeloid leukemia, or CML, is a clonal disorder in which the leukemic stem cell gives rise to red cells, neutrophils, eosinophils, basophils, monocyte-macrophages, platelets, T cells and B cells. A reciprocal translocation between chromosomes 9 and 22 results in a shortened chromosome 22, called the Philadelphia chromosome ($Ph^1$) Although up to 10% of CML cases had been classified as Ph negative, such cases are now considered very rare.

This translocation generates a fused gene bcr-abl, the product of which (p210) plays an important role in tumorigenesis. This cytoplasmic protein has about 1910 amino acid residues and includes exons 2 and 3 of bcr and exon 2 of abl. Despite efforts directed at inhibiting the synthesis of bcr-abl using antisense constructs, it appears that the tumorigenic phenotype of Ph positive cells returns shortly after treatments.

The present invention relates to antisense oligonucleotides and polynucleotides directed to portions of the Grb2 and Crkl genes and their use in the treatment of cancer. It is believed that the Grb2 and Crkl gene products both interact with the bcr-abl product and, therefore, participate in the transformation of CML cells. Inhibiting the synthesis of these molecules reduces tumor cell growth. In particular, it is contemplated that using these antisense molecules, either alone or in conjunction with other antisense molecules, it is possible to effectively treat CML, and possibly other cancers. The oligo- or polynucleotides themselves, or expression vectors encoding therefor, may be employed. The preferred method of delivering these nucleic acids is via liposomes. The invention, in its various embodiments, is described in greater detail, below.

B. Polynucleotides and Oligonucleotides

The term "antisense" is intended to refer to polynucleotide molecules complementary to a portion of a Grb2 or Crkl RNA, or the DNA's corresponding thereto. See FIGS. 4 and 5. "Complementary" polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

The intracellular concentration of monovalent cation is approximately 160 mM (10 mM $Na^+$; 150 mM $K^+$). The intracellular concentration of divalent cation is approximately 20 mM (18 mM $Mg^+$; 2 mM $Ca^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that the most effective antisense constructs for the present invention will include regions complementary to the mRNA start site. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean polynucleotides that are substantially complementary over their entire length and have very few base mismatches. For example, sequences of fifteen bases in length may be termed complementary when they have a complementary nucleotide at thirteen or fourteen nucleotides out of fifteen. Naturally, sequences which are "completely complementary" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

The polynucleotides according to the present invention may encode an Grb2 or Crkl gene or a portion of those genes that is sufficient to effect antisense inhibition of protein expression. The polynucleotides may be derived from genomic DNA, i.e., cloned directly from the genome of a particular organism. In other embodiments, however, the polynucleotides may be complementary DNA (cDNA). cDNA is DNA prepared using messenger RNA (mRNA) as template. Thus, a cDNA does not contain any interrupted coding sequences and usually contains almost exclusively the coding region(s) for the corresponding protein. In other embodiments, the antisense polynucleotide may be produced synthetically.

It may be advantageous to combine portions of the genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

The DNA and protein sequences for Grb2 and Crkl are published in the literature by Lowenstein et al. (1992) and ten Hoeve et al. (1993), respectively, both of which are incorporated herein by reference. It is contemplated that natural variants of exist that have different sequences than those disclosed herein. Thus, the present invention is not limited to use of the provided polynucleotide sequence for Grb2 and Crkl but, rather, includes use of any naturally-occurring variants. Depending on the particular sequence of such variants, they may provide additional advantages in terms of target selectivity, i.e., avoid unwanted antisense inhibition of related transcripts. The present invention also encompasses chemically synthesized mutants of these sequences.

As stated above, although the antisense sequences may be full length genomic or cDNA copies (see FIGS. 4 and 5), or large fragments thereof, they also may be shorter fragments, or "oligonucleotides," defined herein as polynucleotides of 50 or less bases. Although shorter oligomers (8–20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45 or 50 base pairs will be used. While all or part of the gene sequence may be employed in the context of antisense construction, statistically, any sequence of 17 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" is refers to an RNA-based enzyme capable of targeting and cleaving particular base sequences in both DNA and RNA. Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense polynucleotide. Ribozyme sequences also may be modified in much the same way as described for antisense polynucleotide. For example, one could incorporate non-Watson-Crick bases, or make mixed RNA/DNA oligonucleotides, or modify the phosphodiester backbone, or modify the 2'-hydroxy in the ribose sugar group of the RNA.

Alternatively, the antisense oligo- and polynucleotides according to the present invention may be provided as RNA via transcription from expression constructs that carry nucleic acids encoding the oligo- or polynucleotides. Throughout this application, the term "expression construct" is meant to include any type of genetic construct containing a nucleic acid encoding an antisense product in which part or all of the nucleic acid sequence is capable of being transcribed. Typical expression vectors include bacterial plasmids or phage, such as any of the pUC or Bluescript™ plasmid series or, as discussed further below, viral vectors adapted for use in eukaryotic cells.

In preferred embodiments, the nucleic acid encodes an antisense oligo- or polynucleotide under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding the inhibitory peptide is not believed to be important, so long as it is capable of expressing the peptide in the targeted cell. Thus, where a human cell is targeted, it is preferable to position the nucleic acid coding the inhibitory peptide adjacent to and under the control of a promoter that is active in the human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of various proteins. The use of other viral or mammalian cellular or bacterial phage promoters which are well-known in the art to achieve expression of peptides according to the present invention is contemplated as well, provided that the levels of expression are sufficient for a given purpose.

By employing a promoter with well-known properties, the level and pattern of expression of an antisense oligo- or polynucleotide can be optimized. Further, selection of a promoter that is regulated in response to specific physiologic signals can permit inducible expression of an inhibitory protein. For example, a nucleic acid under control of the human PAI-1 promoter results in expression inducible by tumor necrosis factor. Tables 2 and 3 list several elements/promoters which may be employed, in the context of the present invention, to regulate the expression of antisense constructs. This list is not intended to be exhaustive of all the possible elements involved in the promotion of expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding an NF-IL6 inhibitory peptide in an expression construct (Table 1 and Table 2). Additionally any promoter/enhancer combination (as per the Eukaryotic Promoter Data Base EPDB) also could be used to drive expression of a nucleic acid according to the present invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 2

| Element | Inducer |
| --- | --- |
| MT II | Phorbol Ester (TPA) Heavy metals |
| MMTV (mouse mammary tumor virus) | Glucocorticoids |
| β-Interferon | poly(rI)X poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester (TPA) |
| Tumor Necrosis Factor | PHA |
| Thyroid Stimulating Hormone α Gene | Thyroid Hormone |

In certain embodiments of the invention, the delivery of a nucleic acid in a cell may be identified in vitro or in vivo by including a marker in the expression construct. The marker would result in an identifiable change to the transfected cell permitting easy identification of expression. Enzymes such as herpes simplex virus thymidine kinase (tk) (eukaryotic) or chloramphenicol acetyltransferase (CAT) (prokaryotic) may be employed.

One also may include a polyadenylation signal to effect proper polyadenylation of the transcript. The nature of the polyadenylation signal is not believed to be crucial to the successful practice of the invention, and any such sequence may be employed. For example, the SV40, β-globin or adenovirus polyadenylation signal may be employed. Also contemplated as an element of the expression cassette is a terminator. These elements can serve to enhance message levels and to minimize read through from the cassette into other sequences.

C. Liposomal Formulations

In a preferred embodiment of the invention, the antisense oligo- or polynucleotides and expression vectors may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are cationic lipid-nucleic acid complexes, such as lipofectamine-nucleic acid complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY-YX.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be reconstituted in a solution of nucleic acid and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentration and stored at 4° C. until use.

In a preferred embodiment, the lipid dioleoylphosphatidylcholine is employed. Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

D. Alternative Delivery Systems

Retroviruses. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a Grb2 or Crkl antisense construct is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing an inserted DNA, together with the retroviral LTR and Ψ sequences, is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Adenoviruses: Human adenoviruses are double-stranded DNA tumor viruses with genome sizes of approximate 36 kB (Tooze, 1981). As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, et al., 1977) have been developed to provide the essential viral proteins in trans.

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Surprisingly persistent expression of transgenes following adenoviral infection has also been reported.

Other Viral Vectors as Expression Constructs. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-viral Methods. Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an Grb2 or Crkl construct may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding a Grb2 or Crkl construct may be delivered via this method.

E. Pharmaceutical Compositions and Routes of Administration

Where clinical application of liposomes containing antisense oligo- or polynucleotides or expression vectors is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the antisense expression vector encapsulated in a liposome as discussed above, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance. For the instant application, it is envisioned that the amount of therapeutic composition comprising a unit dose will range from about 5–30 mg of polynucleotide.

F. Clinical Protocols

Typically, patients that are candidates for treatment are those in the chronic phase of CML. About 7,000 new patients per year are diagnosed with CML, and the median duration of the chronic phase of the disease lasts for five years. The typical course of treatment will be given in eight week cycles, although longer duration may be used if no adverse effects are observed with the patient, and shorter terms of treatment may result if the patient does not tolerate the treatment as hoped. Each cycle will consist of between 20 and 35 individual doses spaced equally, although this too may be varied depending on the clinical situation.

G. EXAMPLES

Example 1

Synthesis of Oligonucleotides

Nuclease-resistant p-ethoxy oligonucleotides were purchased from Oligos Etc. (Willsonville, Oreg.). The length of the oligonucleotides range between 16 to 18 bases. The sequences of the oligonucleotides, from 5' to 3', are as follows:

1. Antisense oligonucleotide targeting the translation initiation site of Grb2: ATATTTGGCGATGGCTTC
2. Antisense oligonucleotide targeting the translation initiation site of Crkl: GTCGAACCGGCGGAGGA
3. Control oligos: GAAGGGCTTCTGCGTC Example 2

Liposome Formation

The lipid, dioleoylphosphatidylchoine, was purchased from Avanti Polar Lipids, Inc. (Alabaster Ala.). Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

Example 3

Oligonucleotide Inhibition of Cell Proliferation (Grb2)

The CML cell lines BV173 and K562 were employed to test the ability of oligonucleotides to inhibit cell growth. These cell lines were originally obtained from human CML patients in blast crisis. Both cell lines express the $p210^{Bcr-Abl}$ fusion protein. HL60 cells, which were originally obtained from a human promyelocytic patient, were used as a control as these cells do not produce bcr-abl, and their proliferation is independent of the ras-signaling pathway.

Five thousand K562 cells, ten thousand BV173 cells, or ten thousand HL60 cells were plated per well in a 96-well plate in 0.1 mL of RPMI 1640 medium containing 10% fetal calf serum. After 2 h of plating, final concentrations of 0–10 µM of liposomal-oligonucleotides were added to these cells. The cells were incubated with liposomal-oligonucleotides for 3 days. The effects of the liposomal-oligonucleotides on the proliferation of the leukemic cells were tested by the alamarBlue (Alamar, Sacramento, Calif.) assay.

AlamarBlue is an oxidation/reduction indicator dye in which absorbency is related to cellular metabolic reduction. Therefore, it is a measure of both cell number and metabolic activity of the cells. After incubation with liposomal-oligonucleotides, 50 µL aliquoted of cells/well were added to 130 µL of medium. Twenty µL of alamarBlue dye were added to each well. After incubation for 6–8 h at 37° C., the plates were read directly on a microplate reader (Molecular Devices, Menlo Park, Calif.) at 570 and 595 nm. The difference in absorbency between 570 and 595 nm was taken as the overall absorbency value of the leukemic cells. The viabilities of liposomal-oligonucleotide-treated cells were compared with those of the untreated cells.

Liposomal-antisense oligonucleotides specific for Grb2 can inhibit the proliferation of leukemic cells in a dose-dependent manner. When 5–7 µM concentrations of liposomal-antisense oligonucleotides specific for Grb2 were used (FIG. 1), the viabilities of the CML cell lines BV173 and K562 were 10–60% of that of untreated cells. In other words 40–90% growth inhibition was induced in CML cells. Under identical conditions, the cell viabilities of HL60 cells were not reduced. In fact, the viabilities of HL60 cells were not reduced until concentrations of 8–10 µM were employed.

Example 4

Oligonucleotide Inhibition of Cell Proliferation (Crkl)

Figure 2:
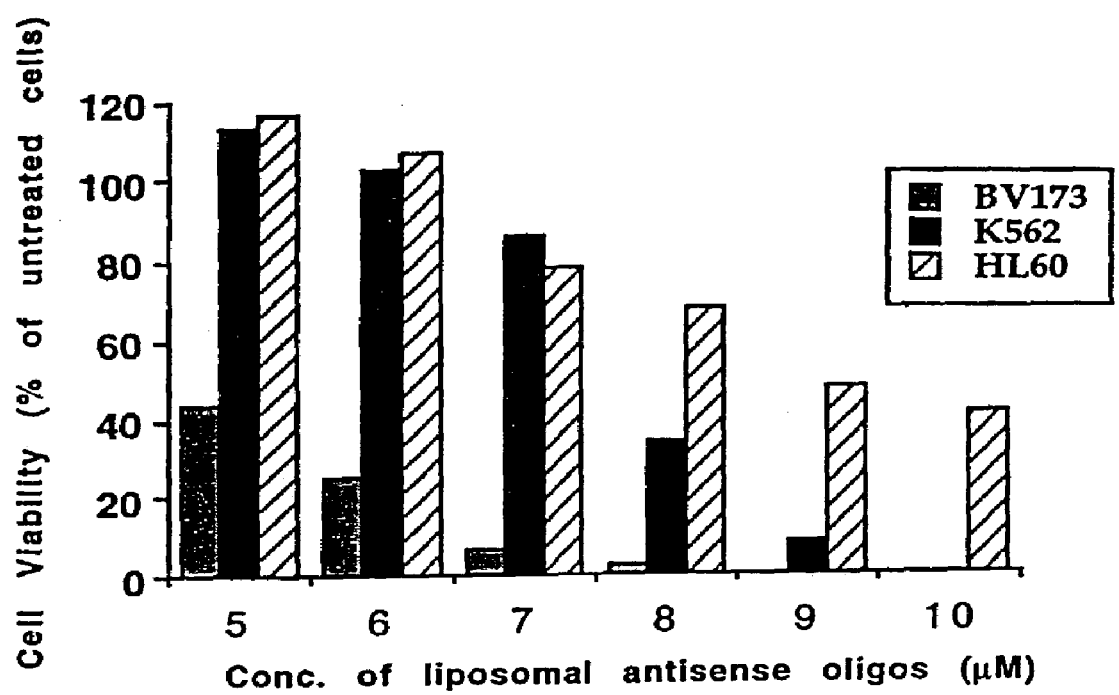
FIG. 2: Effects of Liposomal Antisense Oligonucleotides Specific for Crkl on Leukemic Cell Growth. BV173, K562 and HL60 cells were incubated with increasing concentrations of liposomal-antisense oligonucleotides specific for Crkl. After three days of incubation, an alamarBlue assay was done to determine the growth-inhibitory effects of these oligonucleotides on the leukemic cells. Viability was expressed as a percentage of untreated cells, which was determined by (absorbance of treated cells/absorbance of untreated cells)×100.
Figure 3:
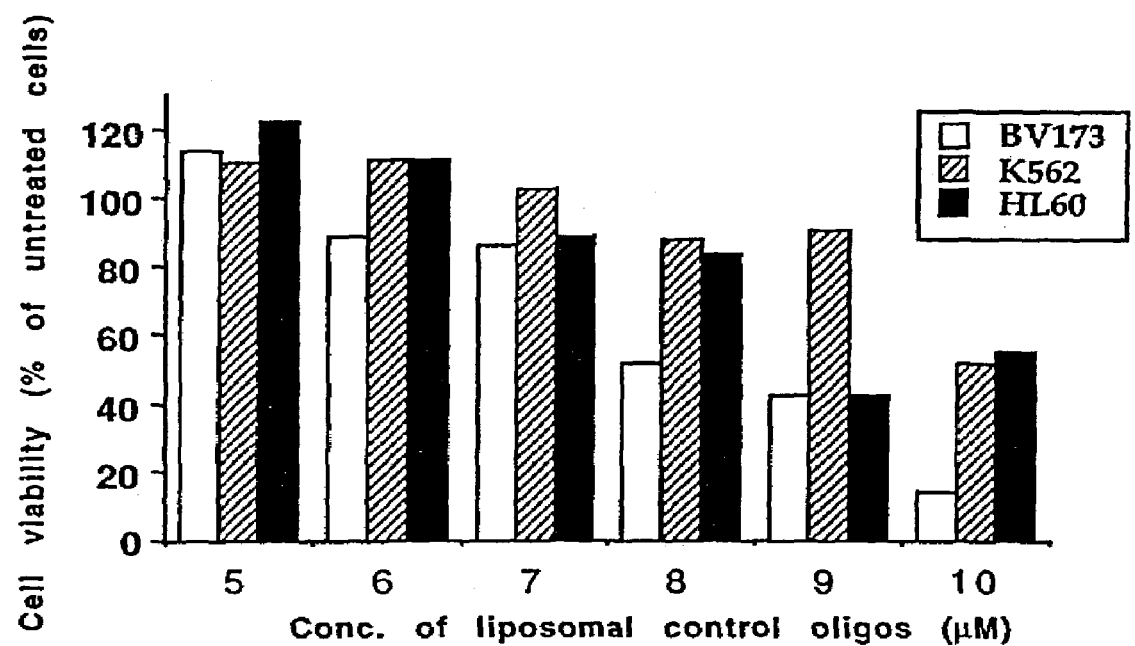
FIG. 3: Effects of Liposomal Control Oligonucleotides on Leukemic Cell Growth. BV173, K562 and HL60 cells were incubated with increasing concentrations of liposomal-control oligonucleotides. After three days of incubation, an alamarBlue assay was done to determine the growth-inhibitory effects of these oligonucleotides on the leukemic cells. Viability was expressed as a percentage of untreated cells, which was determined by (absorbance of treated cells)/(absorbance of untreated cells)×100.

The assay was conducted as described in Example 5. Liposomal-antisense oligonucleotides specific for Crkl can inhibit the proliferation of leukemic cells in a dose-dependent manner. When 5–8 µM concentrations of liposomal-antisense oligonucleotides specific for Crkl were used (FIG. 2), the viabilities of BV173 cells were 10–40% of that of untreated cells. When 8–9 µM concentrations of liposomal-antisense oligonucleotides were used, the viabilities of K562 cells were 10–40% of untreated cells. The cell viabilities of HL60 cells were not reduced to 40%, except when 10 µM concentrations of liposomal-antisense oligonucleotides were used.

Example 5

Oligonucleotide Inhibition of Cell Proliferation (Control)

Liposomal-control oligonucleotides that do not hybridize to Grb2 or Crkl sequences do not inhibit the proliferation of CML cells except at high concentrations. The viabilities of BV173 cells were reduced by 50% when 8 µM or greater concentrations of liposomal-control oligos were used. The viabilities of K562 and HL60 cells were not reduced except at 10 µM concentrations.

H. REFERENCES

The following references, to the extent that they provide exemplary procedural or other details supplementary to those set forth herein, are specifically incorporated herein by reference:

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Bangham et al., *J. Mol. Biol.* 13:238–52 (1965)

Bedi et al., "Inhibition of apoptosis by Bcr-Abl in chronic myeloid leukemia," *Blood*, 83:2038–2044, 1994.

Benvenisty and Neshif, "Direction introduction of genes into rats and expression of the genes," *Proc. Natl. Acad. Sci. USA*, 83:9551–9555, 1986.

Boussif et al., 1995

Chang et al., "Foreign gene delivery and expression in hepatocytes using a hepatitis B virus vector," *Hepatology*, 14:134A, 1991.

Chen and Okayama, "High-efficiency transfection of mammalian cells by plasmid DNA," *Mol. Cell Biol.*, 7:2745–2752, 1987.

Coffin, "Retroviridae and their replication," In: *Virology*, Fields et al. (eds.), New York: Raven Press, pp. 1437–1500, 1990.

Coupar et al., "A general method for the construction of recombinant vaccinia virus expressing multiple foreign genes," *Gene*, 68:1–10, 1988.

Deamer and Uster, 1983

Dubensky et al., "Direct transfection of viral and plasmid DNA into the liver or spleen of mice," *Proc. Nat'l Acad. Sci. USA*, 81:7529–7533, 1984.

Fechheimer et al., "Transfection of mammalian cells with plasmid DNA by scrape loading and sonication loading," *Proc. Nat'l Acad. Sci. USA*, 84:8463–8467, 1987.

Fraley et al., "Entrapment of a bacterial plasmid in phospholipid vesicles: Potential for gene transfer," *Proc. Nat'l Acad. Sci. USA*, 76:3348–3352, 1979.

Friedmann, "Progress toward human gene therapy," *Science*, 244:1275–1281, 1989.

Ghosh and Bachhawat, "Targeting of liposomes to hepatocytes," In: Wu G, Wu C ed., Liver diseases, targeted diagnosis and therapy using specific receptors and ligands, New York: Marcel Dekker, pp. 87–104, 1991.

Gopal, "Gene transfer method for transient gene expression, stable transfection, and cotransfection of suspension cell cultures," *Mol. Cell Biol.*, 5:1188–1190, 1985.

Graham and van der Eb, "A new technique for the assay of infectivity of human adenovirus 5 DNA", *Virology*, 52:456–467, 1973.

Graham et al., "Characteristics of a human cell line transformed by DNA from human adenovirus type 5", *J. Gen. Virol.*, 36:59–72, 1977.

Gregoriadis, *DRUG CARRIERS IN BIOLOGY AND MEDICINE*, G. Gregoriadis ed. (1979)

Grunhaus and Horwitz, "Adenovirus as cloning vector," *Seminar in Virology*, 3:237–252, 1992.

Harland and Weintraub, "Translation of mammalian mRNA injected into Xenopus oocytes is specifically inhibited by antisense RNA," *J. Cell Biol.*, 101:1094–1099, 1985.

Hermonat and Muzycska, "Use of adenoassociated virus as a mammalian DNA cloning vector: Transduction of neomycin resistance into mammalian tissue culture cells," *Proc. Natl. Acad. Sci. USA*, 81:6466–6470, 1984.

Horwich et al., "Synthesis of hepadenovirus particles that contain replication-defective duck hepatitis B virus genomes in cultured HuH7 cells," *J. Virol.*, 64:642–650, 1990.

Kaneda et al., "Increased expression of DNA cointroduced with nuclear protein in adult rat liver," *Science*, 243: 375–378, 1989.

Kato et al., "Expression of hepatitis B virus surface antigen in adult rat liver," *J. Biol. Chem.*, 266:3361–3364, 1991.

Klein et al., "High-velocity microprojectiles for delivering nucleic acids into living cells," *Nature*, 327:70–73, 1987.

Lowenstein et al., "The SH2 and SH3 domain-containing protein Grb2 links receptor tyrosine kinases to ras signalling," *Cell*, 70:431–442, 1992.

Mann et al., "Construction of a retrovirus packaging mutant and its use to produce helper-free defective retrovirus," *Cell*, 33:153–159, 1983.

McGahon et al., "Bcr-Abl maintains resistance of chronic myelogneous leukemia cells to apoptotic cell death," *Blood*, 83:1179–1187, 1994.

Nicolas and Rubenstein, "Retroviral vectors," In: *Vectors: A survey of molecular cloning vectors and their uses*, Rodriguez and Denhardt (eds.), Stoneham: Butterworth, pp. 494–513, 1988.

Nicolau et al., "Liposomes as carriers for in vivo gene transfer and expression," *Methods Enzymol.*, 149:157–176, 1987.

Nicolau and Sene, "Liposome-mediated DNA transfer in eukaryotic cells," *Biochem. Biophys. Acta*, 721:185–190, 1982.

Paskind et al., "Dependence of moloney murine leukemia virus production on cell growth," *Virology*, 67:242–248, 1975.

Pendergast et al., "Bcr-Abl-induced oncogenesis is mediated by direct interaction with the SH2 domain of the GRB-2 adaptor protein," Cell, 75:175–185.

Potter et al., "Enhancer-dependent expression of human k immunoglobulin genes introduced into mouse pre-B lymphocytes by electroporation," Proc. Nat'l Acad. Sci. USA, 81:7161–7165, 1984.

Puil et al., "Bcr-Abl oncoproteins bind directly to activators of the ras signaling pathway," EMBO J., 13(4):764–773, 1994.

Ridgeway, "Mammalian expression vectors," In: Rodriguez R L, Denhardt D T, ed. Vectors: A survey of molecular cloning vectors and their uses. Stoneham: Butterworth, pp. 467–492, 1988.

Rippe et al., "DNA-mediated gene transfer into adult rat hepatocytes in primary culture," Mol. Cell Biol., 10:689–695, 1990.

Skorski et al., "Phosphatidylinositol-3 kinase activity is regulated by BCR/ABL and is required for the growth of Philadelphia chromosome-positive cells," Blood, 86:726–736, 1995.

Skorski et al., "Negative regulation of p120$^{GAP}$ GTPase promoting activity by p210$^{Bcr-Abl}$: Implication for RAS-dependent Philadelphia chromosome positive cell growth," J. Exp. Med., 179:1855–1865, 1994.

Skorski et al., "Suppression of Philadelphia leukemia cell growth in mice by Bcr-Abl antisense oligodeoxynucleotides," Proc. Natl. Acad. Sci. USA, 91:4504–4508, 1994.

Stratford-Perricaudet and Perricaudet, "Gene transfer into animals: the promise of adenovirus," p. 51–61, In: Human Gene Transfer, Eds, O. Cohen-Haguenauer and M. Boiron, Editions John Libbey Eurotext, France, 1991.

Szoka and Papahadjopoulos, 1978

Szczylik et al., "Selective inhibition of Leukemia cell proliferation by BCR-ABL antisense oligonucleotides," Science, 253:562–265, 1991.

Tari et al., "Liposomal delivery of methylphosphonate oligodeoxynucleotides in chronic myelogenous leukemia," Blood, 84:601–607, 1994.

ten Hoeve et al., "Tyrosine phosphorylation of CRKL in Philadelphia+ leukemia," Blood, 84:1731-1736, 1994.

ten Hoeve et al., "Cellular interactions of CRKL, an SH2-SH3 adaptor protein," Cancer Res., 54:2563–2567, 1994.

ten Hoeve et al., "Isolation and chromosomal localization of CRKL, a human CRK-like gene," Oncogene, 8:2469–2475, 1993.

Temin, "Retrovirus vectors for gene transfer: Efficient integration into and expression of exogenous DNA in vertebrate cell genome," In: Gene Transfer, Kucherlapati (ed.), New York: Plenum Press, pp. 149–188, 1986.

Tooze, 1981

Tur-Kaspa et al., "Use of electroporation to introduce biologically active foreign genes into primary rat hepatocytes," Mol. Cell Biol., 6:716–718, 1986.

Wagner et al., Science, 260:1510–1513, 1993.

Wong et al., "Appearance of β-lactamase activity in animal cells upon liposome mediated gene transfer," Gene, 10:87–94, 1980.

Wu and Wu, "Evidence for targeted gene delivery to HepG2 hepatoma cells in vitro," Biochemistry, 27:887–892, 1988.

Wu and Wu, "Receptor-mediated in vitro gene transfections by a soluble DNA carrier system," J. Biol. Chem., 262: 4429–4432, 1987.

Yang et al., "in vivo and in vitro gene transfer to mammalian somatic cells by particle bombardment," Proc. Nat'l Acad. Sci. USA, 87:9568–9572, 1990.

Zelenin et al., "High-velocity mechanical DNA transfer of the chloramphenicol acetyltransferase gene into rodent liver, kidney and mammary gland cells in organ explants and in vivo," FEBS Lett., 280:94–96, 1991.

---

What is claimed is:

1. A composition comprising:
   a) an oligonucleotide having the sequence ATATTTGGCGATGGCTTC (SEQ ID NO:5), and
   b) a neutral lipid,
wherein said oligonucleotide inhibits the expression of Grb2.

2. The composition of claim 1, wherein said lipid is a phospholipid.

3. The composition of claim 1, wherein said lipid comprises the lipid dioleoylphosphatidylcholine.

4. The composition of claim 1, further comprising a polynucleotide that hybridizes to a bcr-abl-encoding polynucleotide.

5. A composition comprising an expression construct that encodes an oligonucleotide having the sequence ATATTTGCGATGGCTTC (SEQ ID NO:5) and a neutral lipid, wherein said oligonucleotide is under the control of a promoter that is active in eukaryotic cells and wherein said composition inhibits the expression of Grb2.

* * * * *

UNITED STATES PATENT AND TRADEMARK OFFICE
CERTIFICATE OF CORRECTION

| | | |
|---|---|---|
| PATENT NO. | : 7,220,853 B2 | Page 1 of 1 |
| APPLICATION NO. | : 10/327509 | |
| DATED | : May 22, 2007 | |
| INVENTOR(S) | : Gabriel Lopez-Berestein et al. | |

It is certified that error appears in the above-identified patent and that said Letters Patent is hereby corrected as shown below:

In column 3, line 47, delete "FIG. 4: cDNA and Protein Sequence of GRB2." and insert --FIG. 4: Contiguous cDNA (SEQ ID NO:1) and Protein Sequence (SEQ ID NO:2) of GRB2.-- therefor.

In column 3, line 50, delete "(SEQ ID NO:1)".

In column 3, line 51, delete "FIG. 5: cDNA and Protein Sequence of CRKL." and insert --FIG. 5: Contiguous cDNA (SEQ ID NO:3) and Protein Sequence (SEQ ID NO:4) of CRKL.-- therefor.

In column 3, lines 54-55, delete "(SEQ ID NO:2)".

In column 16, line 2, after "ATATTTGGCGATGGCTTC", insert --(SEQ ID NO:5)--.

In column 16, line 4, after "GTCGAACCGGCGGAGGA", insert --(SEQ ID NO:6)--.

In column 16, line 5, after "GAAGGGCTTCTGCGTC", insert --(SEQ ID NO:7)--.

Signed and Sealed this
Twenty-second Day of March, 2011

David J. Kappos
*Director of the United States Patent and Trademark Office*

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 1109 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 79..729

(xi) SEQUENCE DESCRIPTION: SEQ ID NO: 1:

```
GCCAGTGAAT TCGGGGGCTC AGCCCTCCTC CCTCCCTTCC CCCTGCTTCA GGCTGCTGAG        60

CACTGAGCAG CGCTCAGA ATG GAA GCC ATC GCC AAA TAT GAC TTC AAA GCT        111
                   Met Glu Ala Ile Ala Lys Tyr Asp Phe Lys Ala
                     1               5                  10

ACT GCA GAC GAC GAG CTG AGC TTC AAA AGG GGG GAC ATC CTC AAG GTT        159
Thr Ala Asp Asp Glu Leu Ser Phe Lys Arg Gly Asp Ile Leu Lys Val
         15                  20                  25
```

```
TTG AAC GAA GAA TGT GAT CAG AAC TGG TAC AAG GCA GAG CTT AAT GGA      207
Leu Asn Glu Glu Cys Asp Gln Asn Trp Tyr Lys Ala Glu Leu Asn Gly
         30                  35                  40

AAA GAC GGC TTC ATT CCC AAG AAC TAC ATA GAA ATG AAA CCA CAT CCG      255
Lys Asp Gly Phe Ile Pro Lys Asn Tyr Ile Glu Met Lys Pro His Pro
 45                  50                  55

TGG TTT TTT GGC AAA ATC CCC AGA GCC AAG GCA GAA GAA ATG CTT AGC      303
Trp Phe Phe Gly Lys Ile Pro Arg Ala Lys Ala Glu Glu Met Leu Ser
 60                  65                  70                  75

AAA CAG CGG CAC GAT GGG GCC TTT CTT ATC CGA GAG AGT GAG AGC GCT      351
Lys Gln Arg His Asp Gly Ala Phe Leu Ile Arg Glu Ser Glu Ser Ala
             80                  85                  90

CCT GGG GAC TTC TCC CTC TCT GTC AAG TTT GGA AAC GAT GTG CAG CAC      399
Pro Gly Asp Phe Ser Leu Ser Val Lys Phe Gly Asn Asp Val Gln His
                 95                 100                 105

TTC AAG GTG CTC CGA GAT GGA GCC GGG AAG TAC TTC CTC TGG GTG GTG      447
Phe Lys Val Leu Arg Asp Gly Ala Gly Lys Tyr Phe Leu Trp Val Val
            110                 115                 120

AAG TTC AAT TCT TTG AAT GAG CTG GTG GAT TAT CAC AGA TCT ACA TCT      495
Lys Phe Asn Ser Leu Asn Glu Leu Val Asp Tyr His Arg Ser Thr Ser
125                 130                 135

GTC TCC AGA AAC CAG CAG ATA TTC CTG CGG GAC ATA GAA CAG GTG CCA      543
Val Ser Arg Asn Gln Gln Ile Phe Leu Arg Asp Ile Glu Gln Val Pro
140                 145                 150                 155

CAG CAG CCG ACA TAC GTC CAG GCC CTC TTT GAC TTT GAT CCC CAG GAG      591
Gln Gln Pro Thr Tyr Val Gln Ala Leu Phe Asp Phe Asp Pro Gln Glu
                160                 165                 170

GAT GGA GAG CTG GGC TTC CGC CGG GGA GAT TTT ATC CAT GTC ATG GAT      639
Asp Gly Glu Leu Gly Phe Arg Arg Gly Asp Phe Ile His Val Met Asp
            175                 180                 185

AAC TCA GAC CCC AAC TGG TGG AAA GGA GCT TGC CAC GGG CAG ACC GGC      687
Asn Ser Asp Pro Asn Trp Trp Lys Gly Ala Cys His Gly Gln Thr Gly
            190                 195                 200

ATG TTT CCC CGC AAT TAT GTC ACC CCC GTG AAC CGG AAC GTC              729
Met Phe Pro Arg Asn Tyr Val Thr Pro Val Asn Arg Asn Val
205                 210                 215

TAAGAGTCAA GAAGCAATTA TTTAAAGAAA GTGAAAAATG TAAAACACAT ACAAAAGAAT    789

TAAACCCACA AGCTGCCTCT GACAGCAGCC TGTGAGGGAG TGCAGAACAC CTGGCCGGGT    849

CACCCTGTGA CCCTCTCACT TTGGTTGGAA CTTTAGGGGG TGGGAGGGGG CGTTGGATTT    909

AAAAATGCCA AAACTTACCT ATAAATTAAG AAGAGTTTTT ATTACAAATT TTCACTGCTG    969

CTCCTCTTTC CCCTCCTTTG TCTTTTTTTT CATCCTTTTT TCTCTTCTGT CCATCAGTGC   1029

ATGACGTTTA AGGCCACGTA TAGTCCTAGC TGACGCCAAT AATAAAAAAC AAGAAACCAA   1089

AAAAAAAAAA CCCGAATTCA                                              1109

(2) INFORMATION FOR SEQ ID NO: 2:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Ala Ile Ala Lys Tyr Asp Phe Lys Ala Thr Ala Asp Asp Glu
 1               5                  10                  15

Leu Ser Phe Lys Arg Gly Asp Ile Leu Lys Val Leu Asn Glu Glu Cys
            20                  25                  30
```

```
Asp Gln Asn Trp Tyr Lys Ala Glu Leu Asn Gly Lys Asp Gly Phe Ile
         35                  40                  45

Pro Lys Asn Tyr Ile Glu Met Lys Pro His Pro Trp Phe Phe Gly Lys
 50                  55                  60

Ile Pro Arg Ala Lys Ala Glu Glu Met Leu Ser Lys Gln Arg His Asp
 65                  70                  75                  80

Gly Ala Phe Leu Ile Arg Glu Ser Glu Ser Ala Pro Gly Asp Phe Ser
                 85                  90                  95

Leu Ser Val Lys Phe Gly Asn Asp Val Gln His Phe Lys Val Leu Arg
                100                 105                 110

Asp Gly Ala Gly Lys Tyr Phe Leu Trp Val Val Lys Phe Asn Ser Leu
                115                 120                 125

Asn Glu Leu Val Asp Tyr His Arg Ser Thr Ser Val Ser Arg Asn Gln
130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175

Phe Arg Arg Gly Asp Phe Ile His Val Met Asp Asn Ser Asp Pro Asn
                180                 185                 190

Trp Trp Lys Gly Ala Cys His Gly Gln Thr Gly Met Phe Pro Arg Asn
                195                 200                 205

Tyr Val Thr Pro Val Asn Arg Asn Val
                210                 215

(2) INFORMATION FOR SEQ ID NO: 3:

(i) SEQUENCE CHARACTERISTICS:
        (A) LENGTH: 1881 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 510..1418

(xi) SEQUENCE DESCRIPTION: SEQ ID NO: 3:

CGGAGGGGGA GGTGGCTGCC GCTTCTCCCG CGTCCGCCAT TTTGTTGCTG TGGCTATTGG      60

GAACAAGCTG GCAAAAGCA CCCCGGAGGC GCGACGCTCC TTCGAGTTCG GTGCCTCGTG      120

TGACGGCGGG GGTCGGTGAA GACCCGTCGA GCTGCGGCGC CGGCGCGTTC CAGGCCGGGA    180

GTCACTGGAG GCACCCCTGG GACGCCGAGC AGCCCGAGAA CCCCGGGGTG GCCTCCGCTG    240

CGGCTCGGGT TTGCCTGCCC CGACCCCCCG GCTCTGCCGT GCATTCCCGG GCGGCTCTCT   300

CCGTGTGGCG GCCCCGGAGC AGGCGGGCGG CGTCGGAGGA TGCTGCGGGC CCGGAGCCGA   360

GAGGAAAGTG CTGGCCCAGC CCTCTGAGCG CTCCTCGAGG TGTGCGAGAG GCCCTTCCTC   420

GGCCCCAAAG CCGTCTGCCG GGCTAAGGCG TGCAGAGCAG GCGAGGACAG CCGCCGCCCC   480

TACCGCCGCA GAGTCCCCGG TCCAACACC ATG TCC TCC GCC AGG TTC GAC TCC     533
                                  Met Ser Ser Ala Arg Phe Asp Ser
                                    1               5

TCG GAC CGC TCC GCC TGG TAT ATG GGG CCG GTG TCT CGC CAG GAG GCG     581
Ser Asp Arg Ser Ala Trp Tyr Met Gly Pro Val Ser Arg Gln Glu Ala
         10                  15                  20

CAG ACC CGG CTC CAG GGC CAG CGC CAC GGT ATG TTC CTC GTC GCG GAT     629
Gln Thr Arg Leu Gln Gly Gln Arg His Gly Met Phe Leu Val Arg Asp
 25                  30                  35                  40
```

-continued

| | | |
|---|---|---|
| TCT TCC ACC TGC CCT GGG GAC TAT GTG CTG TCG GTG TCC GAG AAC TCG<br>Ser Ser Thr Cys Pro Gly Asp Tyr Val Leu Ser Val Ser Glu Asn Ser<br>45 50 55 | | 677 |
| CGG GTC TCC CAC TAC ATT ATC AAC TCG CTG CCC AAC CGC CGT TTT AAG<br>Arg Val Ser His Tyr Ile Ile Asn Ser Leu Pro Asn Arg Arg Phe Lys<br>60 65 70 | | 725 |
| ATC GGG GAC CAG GAA TTT GAC CAT TTG CCG GCC CTG CTG GAG TTT TAC<br>Ile Gly Asp Gln Glu Phe Asp His Leu Pro Ala Leu Leu Glu Phe Tyr<br>75 80 85 | | 773 |
| AAG ATC CAC TAC CTG GAC ACC ACC ACC CTC ATC GAG CCT GCG CCC AGG<br>Lys Ile His Tyr Leu Asp Thr Thr Thr Leu Ile Glu Pro Ala Pro Arg<br>90 95 100 | | 821 |
| TAT CCA AGC CCA CCA ATG GGA TCT GTC TCA GCA CCC AAC CTG CCT ACA<br>Tyr Pro Ser Pro Pro Met Gly Ser Val Ser Ala Pro Asn Leu Pro Thr<br>105 110 115 120 | | 869 |
| GCA GAA GAT AAC CTG GAA TAT GTA CGG ACT CTG TAT GAT TTT CCT GGG<br>Ala Glu Asp Asn Leu Glu Tyr Val Arg Thr Leu Tyr Asp Phe Pro Gly<br>125 130 135 | | 917 |
| AAT GAT GCC GAA GAC CTG CCC TTT AAA AAG GGT GAG ATC CTA GTG ATA<br>Asn Asp Ala Glu Asp Leu Pro Phe Lys Lys Gly Glu Ile Leu Val Ile<br>140 145 150 | | 965 |
| ATA GAG AAG CCT GAA GAA CAG TGG TGG AGT GCC CGG AAC AAG GAT GGC<br>Ile Glu Lys Pro Glu Glu Gln Trp Trp Ser Ala Arg Asn Lys Asp Gly<br>155 160 165 | | 1013 |
| CGG GTT GGG ATG ATT CCT GTC CCT TAT GTC GAA AAG CTT GTG AGA TCC<br>Arg Val Gly Met Ile Pro Val Pro Tyr Val Glu Lys Leu Val Arg Ser<br>170 175 180 | | 1061 |
| TCA CCA CAC GGA AAG CAT GGA AAT AGG AAT TCC AAC AGT TAT GGG ATC<br>Ser Pro His Gly Lys His Gly Asn Arg Asn Ser Asn Ser Tyr Gly Ile<br>185 190 195 200 | | 1109 |
| CCA GAA CCT GCT CAT GCA TAC GCT CAA CCT CAG ACC ACA ACT CCT CTA<br>Pro Glu Pro Ala His Ala Tyr Ala Gln Pro Gln Thr Thr Thr Pro Leu<br>205 210 215 | | 1157 |
| CCT GCA GTT TCC GGT TCT CCT GGG GCA GCA ATC ACC CCT TTG CCA TCC<br>Pro Ala Val Ser Gly Ser Pro Gly Ala Ala Ile Thr Pro Leu Pro Ser<br>220 225 230 | | 1205 |
| ACA CAG AAT GGA CCT GTC TTT GCG AAA GCA ATC CAG AAA AGA GTA CCC<br>Thr Gln Asn Gly Pro Val Phe Ala Lys Ala Ile Gln Lys Arg Val Pro<br>235 240 245 | | 1253 |
| TGT GCT TAT GAC AAG ACT GCC TTG GCA TTA GAG GTT GGT GAC ATC GTG<br>Cys Ala Tyr Asp Lys Thr Ala Leu Ala Leu Glu Val Gly Asp Ile Val<br>250 255 260 | | 1301 |
| AAA GTC ACA AGG ATG AAT ATA AAT GGC CAG TGG GAA GGC GAA GTG AAC<br>Lys Val Thr Arg Met Asn Ile Asn Gly Gln Trp Glu Gly Glu Val Asn<br>265 270 275 280 | | 1349 |
| GGG CGC AAA GGG CTT TTC CCC TTT ACG CAC GTC AAA ATC TTT GAC CCT<br>Gly Arg Lys Gly Leu Phe Pro Phe Thr His Val Lys Ile Phe Asp Pro<br>285 290 295 | | 1397 |
| CAA AAC CCA GAT GAA AAC GAG TGATTGCTGT TGCCCTGTTT CCTGCTGCTT<br>Gln Asn Pro Asp Glu Asn Glu<br>300 | | 1448 |
| TGTTGTTCTG CCTGTCCTAG TCTCCTTTGA AGTGGGAAAG CATTTTCTCT CATAGGCAAG | | 1508 |
| TCACACTGCA TTGCCGAAGT CCAGCTTTCT GCAGACTGGC AGTCGCACAC ACATTTGGAA | | 1568 |
| TGCACACAGC GGCTGCCTCC TGATGTTTGT ATCATAGTCG TATTGTGCAA AGAGTAGCCG | | 1628 |
| ATTTTAGAGT TCTTTTGGAT CATAAACTGG AAATACTGAT GGAAGCACAC AAGTGGAGAG | | 1688 |
| AAGTTGACGT GGAAAGGGTC TTCCTTCTCA TTGCTGCCCG TTTGTACATG GGACTGATTC | | 1748 |
| TGTCGTGTTC ACCAGAGAAA GCTTGAGGCC ATGGCGAGAT ACTGCATGTT TGCTGTTCCA | | 1808 |

```
CAAAGCAGTG GCTTAGCTGC CATCTTGCTT TTCTTTGGAC AACAGGAAGT GAACCTTAAG    1868

GAAGAGAGAA TTC                                                       1881
```

(2) INFORMATION FOR SEQ ID NO: 4:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ser Ser Ala Arg Phe Asp Ser Ser Asp Arg Ser Ala Trp Tyr Met
 1               5                  10                  15

Gly Pro Val Ser Arg Gln Glu Ala Gln Thr Arg Leu Gln Gly Gln Arg
                20                  25                  30

His Gly Met Phe Leu Val Arg Asp Ser Ser Thr Cys Pro Gly Asp Tyr
            35                  40                  45

Val Leu Ser Val Ser Glu Asn Ser Arg Val Ser His Tyr Ile Ile Asn
50                  55                  60

Ser Leu Pro Asn Arg Arg Phe Lys Ile Gly Asp Gln Glu Phe Asp His
65                  70                  75                  80

Leu Pro Ala Leu Leu Glu Phe Tyr Lys Ile His Tyr Leu Asp Thr Thr
                85                  90                  95

Thr Leu Ile Glu Pro Ala Pro Arg Tyr Pro Ser Pro Met Gly Ser
            100                 105                 110

Val Ser Ala Pro Asn Leu Pro Thr Ala Glu Asp Asn Leu Glu Tyr Val
            115                 120                 125

Arg Thr Leu Tyr Asp Phe Pro Gly Asn Asp Ala Glu Asp Leu Pro Phe
            130                 135                 140

Lys Lys Gly Glu Ile Leu Val Ile Ile Glu Lys Pro Glu Glu Gln Trp
145                 150                 155                 160

Trp Ser Ala Arg Asn Lys Asp Gly Arg Val Gly Met Ile Pro Val Pro
                165                 170                 175

Tyr Val Glu Lys Leu Val Arg Ser Ser Pro His Gly Lys His Gly Asn
            180                 185                 190

Arg Asn Ser Asn Ser Tyr Gly Ile Pro Glu Pro Ala His Ala Tyr Ala
            195                 200                 205

Gln Pro Gln Thr Thr Thr Pro Leu Pro Ala Val Ser Gly Ser Pro Gly
            210                 215                 220

Ala Ala Ile Thr Pro Leu Pro Ser Thr Gln Asn Gly Pro Val Phe Ala
225                 230                 235                 240

Lys Ala Ile Gln Lys Arg Val Pro Cys Ala Tyr Asp Lys Thr Ala Leu
                245                 250                 255

Ala Leu Glu Val Gly Asp Ile Val Lys Val Thr Arg Met Asn Ile Asn
            260                 265                 270

Gly Gln Trp Glu Gly Glu Val Asn Gly Arg Lys Gly Leu Phe Pro Phe
            275                 280                 285

Thr His Val Lys Ile Phe Asp Pro Gln Asn Pro Asp Glu Asn Glu
            290                 295                 300
```

-continued (2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 5:

ATATTTGGCG ATGGCTTC          18

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 6:

GTCGAACCGG CGGAGGA          17

(2) INFORMATION FOR SEQ ID NO: 7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 7:

GAAGGGCTTC TGCGTC          16